US010492717B2

(12) United States Patent
Maccabee et al.

(10) Patent No.: US 10,492,717 B2
(45) Date of Patent: Dec. 3, 2019

(54) METHODS, SYSTEMS, AND DEVICES FOR DETERMINING AND VISUALLY INDICATING DEMYELINATED PATHWAYS

(71) Applicant: The Research Foundation of State University of New York, Albany, NY (US)

(72) Inventors: Paul Jacob Maccabee, Hastings-on-Hudson, NY (US); Lawrence Philip Eberle, Elmont, NY (US)

(73) Assignee: The Research Foundation of State University of New York, Albany, NY (US)

( * ) Notice: Subject to any disclaimer, the term of this patent is extended or adjusted under 35 U.S.C. 154(b) by 453 days.

(21) Appl. No.: 15/034,062

(22) PCT Filed: Nov. 4, 2014

(86) PCT No.: PCT/US2014/063956
§ 371 (c)(1),
(2) Date: May 3, 2016

(87) PCT Pub. No.: WO2015/066726
PCT Pub. Date: May 7, 2015

(65) Prior Publication Data
US 2016/0270709 A1 Sep. 22, 2016

Related U.S. Application Data

(60) Provisional application No. 61/899,622, filed on Nov. 4, 2013.

(51) Int. Cl.
*A61B 5/00* (2006.01)
*A61B 5/0492* (2006.01)
(Continued)

(52) U.S. Cl.
CPC ........ *A61B 5/4041* (2013.01); *A61B 5/04012* (2013.01); *A61B 5/0488* (2013.01);
(Continued)

(58) Field of Classification Search
CPC ... A61B 5/0488; A61B 5/0492; A61B 5/4041; A61B 17/00234; A61B 2017/00022
See application file for complete search history.

(56) References Cited

U.S. PATENT DOCUMENTS

2004/0038311 A1* 2/2004 Pestronk ................ C07K 16/44
435/7.2
2005/0113877 A1 5/2005 Spinelli et al.
(Continued)

OTHER PUBLICATIONS

International Search Report and Written Opinion issued (dated Mar. 3, 2015) in corresponding International Application No. PCT/US2014/063956.

*Primary Examiner* — Patrick Fernandes
(74) *Attorney, Agent, or Firm* — Haug Partners LLP

(57) ABSTRACT

A method includes receiving multiple compound muscle action potential values (CMAPs), wherein each CMAP is an onset latency, a peak latency, a conduction velocity, or a response amplitude measured from a baseline; for each of the CMAPs and for each of a number parameters calculated from the CMAPs, determining a corresponding demyelinating boundary value using a normal value from a preselected population; determining whether each of the CMAPs and each of the parameters exceeds the corresponding demyelinating boundary value; determining one or more demyelinated nerve pathways based on which of the CMAPs and the parameters exceeds the corresponding demyelinating boundary value; indicating on a display which of the CMAPs and the parameters exceed the corresponding demyelinating boundary value; and displaying, in pictorial form,
(Continued)

an anatomical diagram indicating the demyelinated nerve pathways.

18 Claims, 9 Drawing Sheets

(51) Int. Cl.
*A61B 5/16* (2006.01)
*A61B 5/04* (2006.01)
*A61B 5/0488* (2006.01)
*A61B 5/11* (2006.01)

(52) U.S. Cl.
CPC ............ *A61B 5/0492* (2013.01); *A61B 5/162* (2013.01); *A61B 5/4052* (2013.01); *A61B 5/6877* (2013.01); *A61B 5/742* (2013.01); *A61B 5/1107* (2013.01)

(56) References Cited

U.S. PATENT DOCUMENTS

| | | | |
|---|---|---|---|
| 2007/0282217 A1* | 12/2007 | McGinnis | A61B 5/0488 600/546 |
| 2008/0071191 A1* | 3/2008 | Kelleher | A61B 5/04001 600/554 |
| 2009/0204175 A1* | 8/2009 | Zanella | A61N 1/36014 607/48 |
| 2010/0222665 A1* | 9/2010 | Roberts | G01R 33/56 600/410 |
| 2010/0286554 A1 | 11/2010 | Davis et al. | |
| 2011/0053956 A1 | 3/2011 | Leahy et al. | |
| 2012/0115138 A1 | 5/2012 | Deigner et al. | |

* cited by examiner

METHODS, SYSTEMS, AND DEVICES FOR DETERMINING AND VISUALLY INDICATING DEMYELINATED PATHWAYS

CROSS REFERENCE TO RELATED APPLICATIONS

This application is filed pursuant to 35 U.S.C. § 371 based on International Application No. PCT/US2014/063956, filed Nov. 4, 2014, which claims the benefit of U.S. Provisional Application No. 61/899,622, filed on Nov. 4, 2013, which is hereby incorporated by reference herein in its entirety.

FIELD

The invention relates to the field of methods, systems, and devices for determining and visually indicating demyelinated nerve pathways. The invention also relates to the methods for evaluating compound muscle action potentials for determining which nerve pathways are demyelinated.

BACKGROUND

In acute and chronic demyelinating peripheral neuropathies, distal peripheral nerve pathways are routinely evaluated using conventional electrical stimulation methods, usually between the knee and ankle and between the elbow and wrist. However, it is the proximal peripheral nerve conducting pathways which are most often implicated as primary and/or the initial pathophysiological targets. Methods of directly assessing conduction in proximal pathways include excitation with either percutaneous high-voltage or direct needle stimulation, which may be painful or inconvenient. Another method uses a magnetic coil (MC) for paravertebral neuromagnetic stimulation over the lower lumbar and sacral spine and is both non-invasive and relatively painless. Neuromagnetic stimulation of proximal conducting pathways can be very useful for measuring and identifying the presence of peripheral neuropathy. Identifying the presence of demyelinating vs non-demyelinating (i.e. axonal) peripheral neuropathy can be important, as the demyelinating form may often be treated, sometimes at great expense, and sometimes with significant side effects.

BRIEF SUMMARY

One embodiment is a non-transitory computer-readable medium, having computer-executable instructions stored thereon, that in response to execution by a device, cause the device to perform operations. The operations include receive multiple compound muscle action potential values (CMAPs), wherein each CMAP is an onset latency, a peak latency, a conduction velocity, or a response amplitude measured from a baseline; for each of the CMAPs and for each of a number parameters calculated from the CMAPs, determine a corresponding demyelinating boundary value using a normal value from a preselected population; determine whether each of the CMAPs and each of the parameters exceeds the corresponding demyelinating boundary value; determine one or more demyelinated nerve pathways based on which of the CMAPs and the parameters exceeds the corresponding demyelinating boundary value; indicate on a display which of the CMAPs and the parameters exceed the corresponding demyelinating boundary value; and display, in pictorial form, an anatomical diagram indicating the demyelinated nerve pathways.

Another embodiment is a computer-based method, wherein actions are performed by a processor operating within a computing device, the actions including receiving multiple compound muscle action potential values (CMAPs), wherein each CMAP is an onset latency, peak latency, conduction velocity, or a response amplitude measured from a baseline; for each of the CMAPs and for each of a number of parameters calculated from the plurality of CMAPs, determining a corresponding demyelinating boundary value using a normal value from a preselected population; determining whether each of the CMAPs and each of the parameters exceeds the corresponding demyelinating boundary value; determining one or more demyelinated nerve pathways based on which of the CMAPs and the parameters exceeds the corresponding demyelinating boundary value; indicating on a display which of the CMAPs and the parameters exceed the corresponding demyelinating boundary value; and displaying, in pictorial form, an anatomical diagram indicating the demyelinated nerve pathways.

Yet another embodiment is a non-transitory computer-readable medium, having computer-executable instructions stored thereon, that in response to execution by a device, cause the device to perform operations. The operations include receive multiple compound muscle action potential values (CMAPs), wherein each CMAP is an onset latency, peak latency, conduction velocity, or a response amplitude measured from a baseline; for each of the CMAPs and for each of a number of parameters calculated from the CMAPs, determine, by regression based on at least one of age or height, a corresponding demyelinating Z regression boundary value using a normal value from a preselected population; determine whether each of the CMAPs and each of the parameters exceeds the corresponding demyelinating Z regression boundary value; determine one or more demyelinated nerve pathways based on which of the CMAPs and the parameters exceeds the corresponding demyelinating regression boundary value; and indicate on a display which of the CMAPs and the parameters exceed the corresponding demyelinating regression boundary value.

Further embodiments include computers and computer systems and networks that include the computer-readable media described above or which are configured and arranged to perform the computer-based method described above.

Throughout the description and claims, the following terms take at least the meanings explicitly associated herein, unless the context dictates otherwise. The meanings identified below do not necessarily limit the terms, but merely provide illustrative examples for the terms. The phrase "an embodiment" as used herein does not necessarily refer to the same embodiment, though it may. In addition, the meaning of "a," "an," and "the" include plural references; thus, for example, "an embodiment" is not limited to a single embodiment but refers to one or more embodiments. Likewise, for example, "a non-transitory computer-readable medium" or "a processor" is not limited to a single "medium" or a single processor but may refer to one or more media (e.g., at least one non-transitory computer-readable medium) or one or more processors (e.g., at least one processor), unless the context clearly dictates otherwise. Similarly, the phrase "one embodiment" does not necessarily refer the same embodiment and is not limited to a single embodiment. As used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3 illustrates one embodiment of an interface for displaying (tibial) soleus CMAP measurements and results, according to some embodiments of the invention;

FIG. 4 illustrates one embodiment of an interface for displaying (femoral) vastus medialis CMAP measurements and results, according to some embodiments of the invention;

FIG. 5 illustrates one embodiment of an interface for displaying (tibial) abductor hallucis CMAP measurements and results, according to some embodiments of the invention;

FIG. 6 illustrates one embodiment of an interface for displaying (peroneal) tibialis anterior CMAP measurements and results, according to some embodiments of the invention;

DETAILED DESCRIPTION

The invention relates to the field of methods, systems, and devices for determining and visually indicating demyelinated nerve pathways. The invention also relates to the methods for evaluating compound muscle action potentials for determining which nerve pathways are demyelinated.

Conventional motor nerve conduction measurements often include median and ulnar nerves in the upper limbs and peroneal and tibial nerves in the lower limbs. These conventional nerve conduction measurements directly evaluate motor pathways between elbow and wrist, and knee and ankle Conventional motor conduction parameters include amplitude, distal latency, motor conduction velocity, and F wave or H-Soleus reflex latency. Magnetic coil stimulation can be used to perform these measurements, stimulating over the motor cortex, cervical spine, and lumbosacral spine. A magnetic coil is placed externally over the stimulation site and then a very brief current pulse is passed through the windings in the coil. The rapidly changing current generates a changing magnetic field that induces a brief electric field (i.e. current) within the body, which excites the target nerve within the body. The activated nerve fibers convey an impulse to a selected target muscle. One or more recording electrodes are placed at each recording site and coupled to a device, such as an electromyography device, for recording results of the stimulation and for determining the latency or conduction velocity at the recording site after stimulation at the stimulation site. Further description and examples of suitable measurement arrangements can be found at, for example, Maccabee, et al., Electromyogr Motor Control Electroencephalogr Clin Neurophysiol 101:153-166 (1996); Maccabee, et al., Muscle Nerve, 43:518-530 (2011); and Matsumoto. et al., Clinical Neurophysiology 124:1055-1067 (2013), all of which are incorporated herein by reference.

Figure 1:
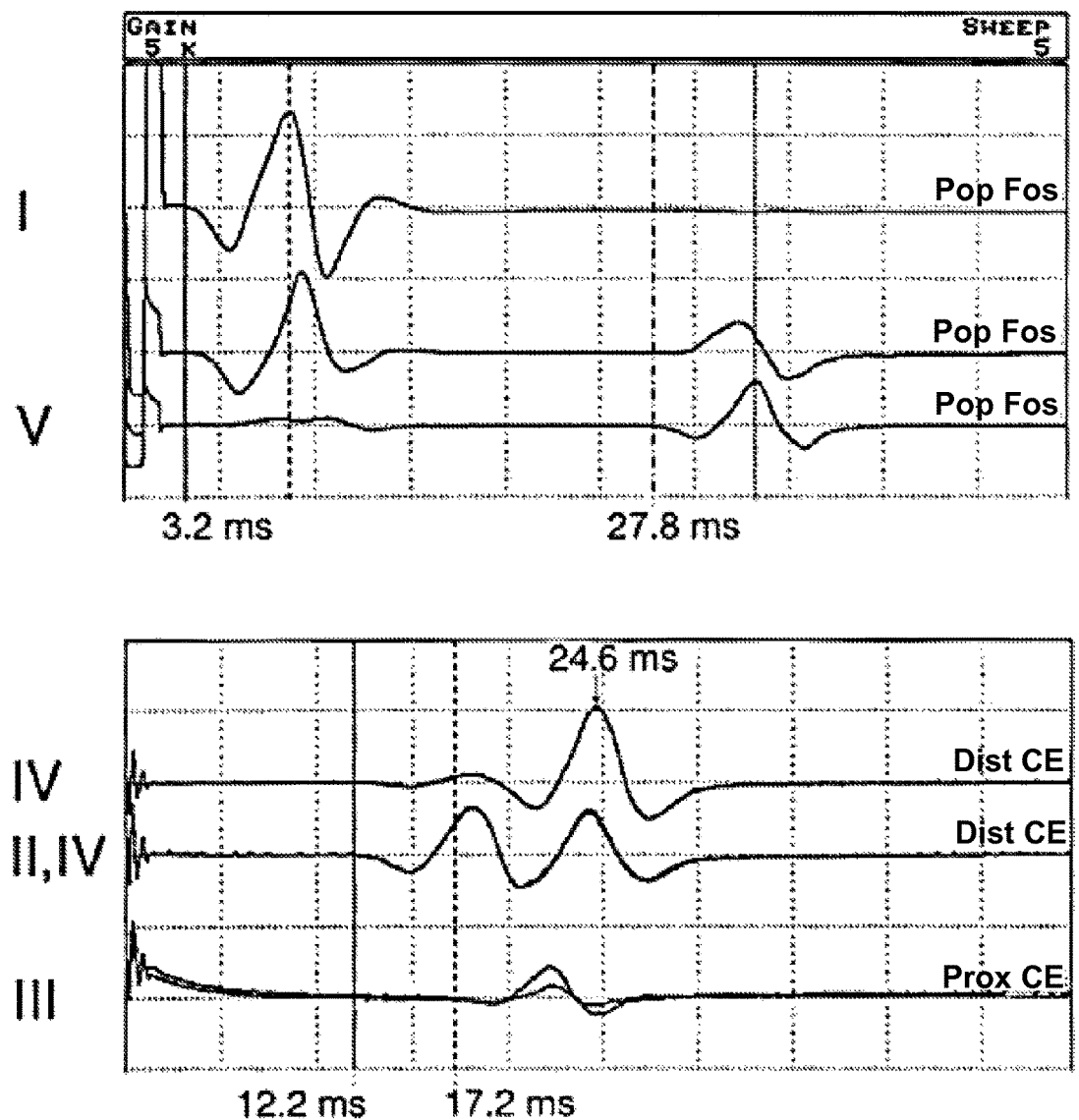
FIG. 1 contains measurements of right soleus compound muscle action potentials (CMAPs) for a 45 year old normal female.
Figure 2:
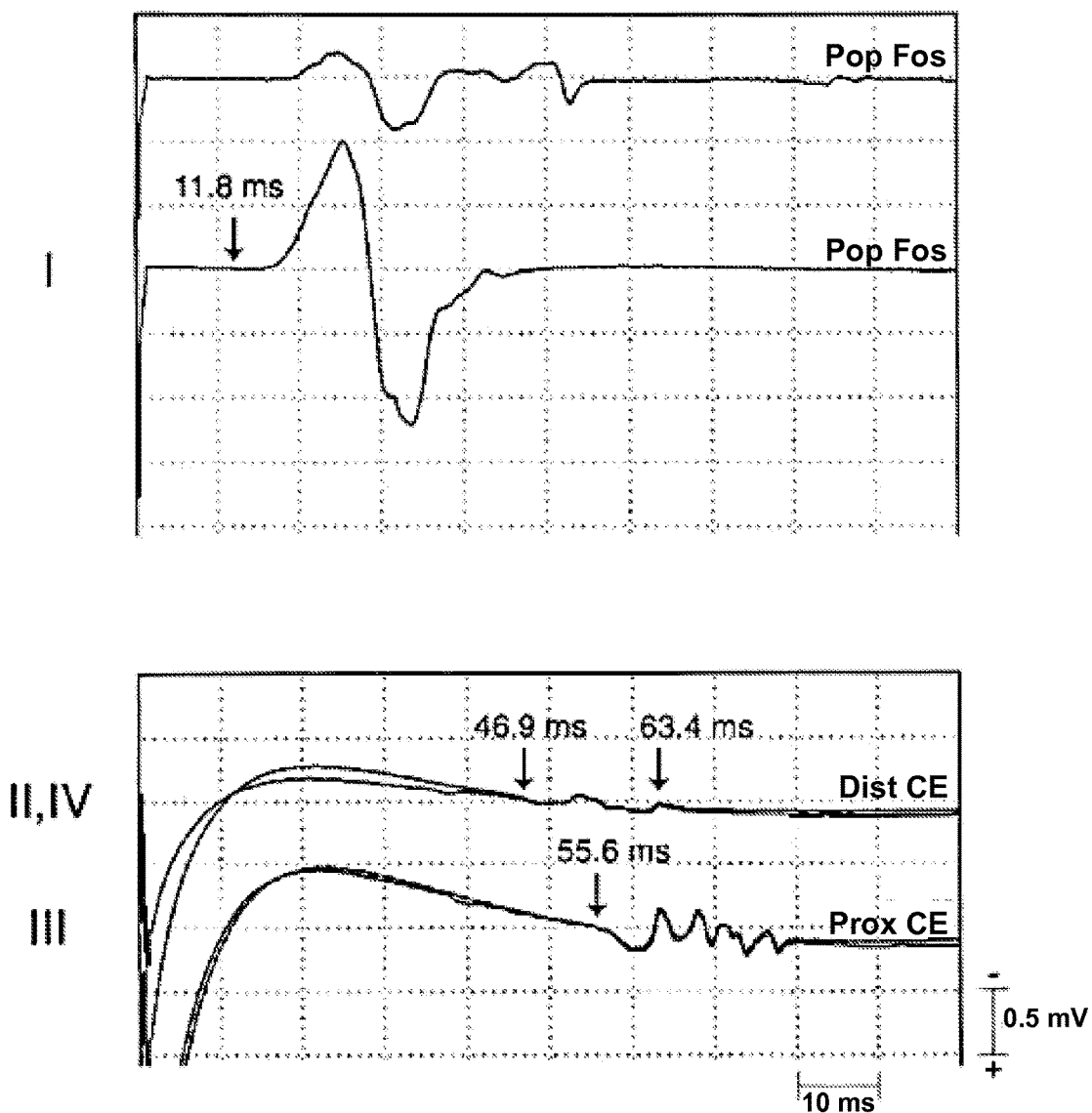
FIG. 2 contains measurements of right soleus compound muscle action potentials for a 30 year old male diagnosed with a chronic demyelinating disorder.

Soleus compound muscle action potentials (CMAPs) can be elicited by cathodal stimulation at popliteal fossa (PF), and neuromagnetic stimulation at distal cauda equina (DCE), and proximal cauda equina (PCE). Absolute and interpotential latencies are designated herein by site of stimulation. Motor CMAPs I, II, III reflect origin at PF, DCE, and PCE, respectively. H-Soleus reflex CMAPs IV and V reflect origin at DCE and PF, respectively. Examples of these CMAPs are illustrated in FIGS. 1 and 2.

One or more CMAP values can be determined including, for example, onset latency, peak latency, conduction velocity, or a response amplitude measured from a baseline. Onset latency can be measured as the origin of the onset positivity at baseline. In at least some embodiments, and as illustrated herein, onset latencies can be obtained for CMAPs I, II, III, and V. In at least some embodiments, a peak latency is more reliably designated for CMAP IV, as its onset may be inconsistently identified as it is often submerged within the tail of the preceding CMAP II. In some embodiments, a response amplitude is measured, for example, from a response baseline to a response negative peak. Other values can be obtained including, for example, inter-potential such as I onset-II onset (soleus upper leg motor conduction time, ULCT), II onset-III onset, III onset-IV peak, and IV peak-V onset (soleus upper leg sensory conduction time, SULCT).

When nerve conduction parameters are above (for latency) or below (for conduction velocity) the limits of normal, for a particular designated population, they can be referred to as in the "axonal range." Latencies within the axonal range can be described as being prolonged and conduction velocities can be described as being slow. Any suitable population can be designated. Unless otherwise indicated, the designated population is the adult human population. Other populations can be designated based on, for example, gender, race, residential location, nationality, ethnicity, age, height, weight, or the like or any combination of these characteristics.

In at least some embodiments, the border for the axonal range is defined as the upper limit of normal (ULN) for latency or the lower limit of normal (LLN) for conduction velocity. When these boundaries are breached, it is possible to refer to a measurement value or parameter as being within the axonal range. The limits of normal can be defined as the normal population mean (for the designated population) plus or minus one or more standard deviations (SDs), for example, 2, 2.5, or 3 standard deviations.

Nerve anatomy distinguishes the central longitudinal axon from the surrounding myelin sheath. Both structures are involved in the conduction mechanism. Typically, primary and exclusive derangement of the axon will result in moderate slowing of conduction velocity and moderate prolongation of conduction time. In-contrast, when latencies are extremely prolonged or when motor conduction velocities are extremely slow, they may be described as being within the "demyelinating range." Thus, nerve conduction measurements may be defined as a continuum, from normal, to axonal, to demyelinating. Often, but not always, these designations confer pathological significance indicative of either axonal or demyelinating change. A clinician may use the full history and neurological exam, as well as the laboratory and imaging studies, to define the presence and classification of peripheral neuropathy.

When evaluating patients with demyelinating peripheral neuropathy, some nerve conduction findings may fall within the axonal range, while other parameters clearly fall within the demyelinating range. In this situation, the parameters within the axonal range may reflect: (i) relatively modest demyelination at the time of the study, (ii) true axonal involvement caused by the demyelinating neuropathy or additional damage from other causes/diseases, or (iii) a combination of both (i) and (ii).

A variety of different methods can be used to define the boundary of the demyelinating range. In some embodiments, the demyelinating range is defined by the latency equaling or exceeding a specified percentage of the ULN (for latency) or by the conduction velocity equaling or less than a specified percentage of the lower LLN (for conduction velocity). For example, the demyelinating boundary may be defined for a latency parameter as 120%, 125%, 130%, 140%, 150% of ULN (for latency) or for conduction velocity as 70%, 75%, or 80% of LLN (for conduction velocity). Other percentage values can be selected for the boundaries or the boundaries can be stated in terms of standard deviations or any other numerical value. In at least some embodiments, a clinician may decide that if a response is above the ULN for a latency (or below the LLN for CV) it is within the axonal range (i.e. prolonged for a latency, and slow for a CV) unless it is beyond the demyelinating boundary for that parameter. This particular method of selecting boundaries for the values and parameters can be referred to as the "percentage approach."

It should be recognized that all of the CMAP values and other parameters described above may have different ULN, LLN, and boundary percentages for defining the axonal range and the demyelinating boundary with respect to that value or parameter.

In some embodiments, a "specificity approach" can be used alternatively or additionally. In at least some instances, the specificity approach determines boundaries that are equivalent to less extreme percentages of the ULN than 150% because proximal conducting pathways are evaluated, which are less affected by variations in temperature and neuropathological degeneration of distal peripheral nerve caused by neuropathy. The specificity approach uses observed outcome comparing populations of patients with axonal vs demyelinating neuropathy. The specificity approach selects boundaries that maintain a specific level, for example, 90%, 95%, 99%, or100%, of specificity with respect to a patient population diagnosed with demyelinating neuropathy. It will be understood that such an approach might only be suitable for instances where there are sufficient patients for evaluation. It should be recognized that, for all of the CMAP values and other parameters described above, a user may employ different specificity percentages for defining the demyelinating boundary with respect to that value or parameter.

As an example, using one patient population, the demyelinating boundary for distal cauda equina latency (recording from foot muscle AHB) was reduced from 45.2 (150% ULN) msec to 36.3 (120.6% ULN) msec using the specificity approach. This reduction in latency markedly improves diagnostic sensitivity while maintaining 100% diagnostic specificity in this instance.

In some embodiments, a "DZR approach" can be used alternatively or additionally, where DZR refers to "demyelinating Z regression." For example, regression analysis can be performed using IBM SPSS statistics, version 21.0. In one embodiment, the input consisted of latency, height, and age for each normal subject for a specific parameter (for example DCE latency). The output linear regression model included a constant, a coefficient for height, a coefficient for age, and the "standard error of the estimate," which, in a regression model, is analogous to a conventional scalar standard deviation.

In the DZR approach, the upper or lower limits of normal (e.g., ULN and LLN) are predicted using linear regression of patient characteristics, such as, for example, height or age or both. The predictions are directly based upon normal data. The predicted boundary is computed for each parameter. If these boundaries are breached, the data is defined as being within the axonal range.

The DZR approach can also be used to calculate a demyelinating boundary, predicted from patient characteristics, such as, for example, height or age or both. The conventional consensus research criteria used to define peripheral nerve demyelination in the clinical laboratory do not take height and age into account. The conventional criteria define the presence of peripheral nerve demyelination as specific percents of the upper limit of normal (ULN) for latencies, or lower limit of normal (LLN) for motor conduction velocity. Nevertheless, it is well documented that height and possibly age significantly impact upon F response latency, motor conduction velocity (CV), and possibly motor terminal latency (TL), the most distal peripheral nerve segment measured by nerve conduction studies.

In at least some embodiments, the DZR approach expresses the conventional demyelinating boundary as a Z score, which is carried over to the regression analysis, and then converted back into msec across a range of heights and age. Regression takes into account any associated increase or decrease of latency with height or age or both.

Specifically, the proposed limits are Z regression standard deviations above or below the regression mean. For each parameter, the demyelinating boundary is calculated for each patient according to their height or age or both. For some latencies, the demyelinating boundary is significantly lower than the "percentage approach" demyelinating boundary because the equivalent of the regression standard deviation (i.e. the "standard error of the estimate") is smaller than the conventional standard deviation.

In at least some embodiments, demyelinating boundaries derived from a normal population are (i) expressed as a Z score which (ii) is carried over to linear regression analysis on height or age or both (now using the regression mean and equivalent regression standard deviation (i.e. the standard error of the estimate) and (iii) converted back into msec across a range of heights.

The following is an example of the DZR approach, using the parameter distal cauda equina latency (DCE latency), at 150% ULN, where ($\overline{X}$)=23.09 msec and (SD)=2.815. Where ULN=mean+2.5 SDs, the ULN is 30.13 msec. Using the "percentage approach," the demyelinating boundary is 150% ULN=45.20 msec.

The demyelinating boundary for DCE latency is transformed into a critical Z score ($Z_c$) by:

$$Z_c = \frac{\text{value} - \overline{X}}{SD} = 7.837$$

where value is 150% ULN, 45.20 milliseconds (msec) in this example. The critical Z score $Z_c$ expresses the demyelinating boundary as the multiple of sample standard deviations deviating from the sample mean. In other words, the demyelinating upper limit for DCE latency at 150% ULN is 7.837 standard deviations from the sample mean in the reference normal population.

In the DZR approach, the sample mean (($\overline{X}$)) is replaced by the sample regression mean, and the sample standard deviation (SD) is replaced by the sample regression standard deviation, referred to as the "standard error of the estimate." The regression mean=constant+(coefficient*height)+ (coefficient*age).

In equation form, DZR demyelinating boundary (msec)= [regression mean]+($Z_c$)*(standard error of the estimate)= [constant+(coefficient*height)+(coefficient*age)]+($Z_c$)* (standard error of the estimate).

Methods, systems, and devices can implement one or more of these approaches and can be used to determine the demyelinating boundaries using one or more approaches and to indicate, visually or pictorially or both, which value, parameters, or sites exhibit indications of demyelination. The methods, systems, and devices described herein may take the form of an entirely hardware embodiment, an entirely software embodiment (which can be disposed, for example, on a non-transitory computer-readable medium), or an embodiment combining software and hardware aspects.

Figure 3:
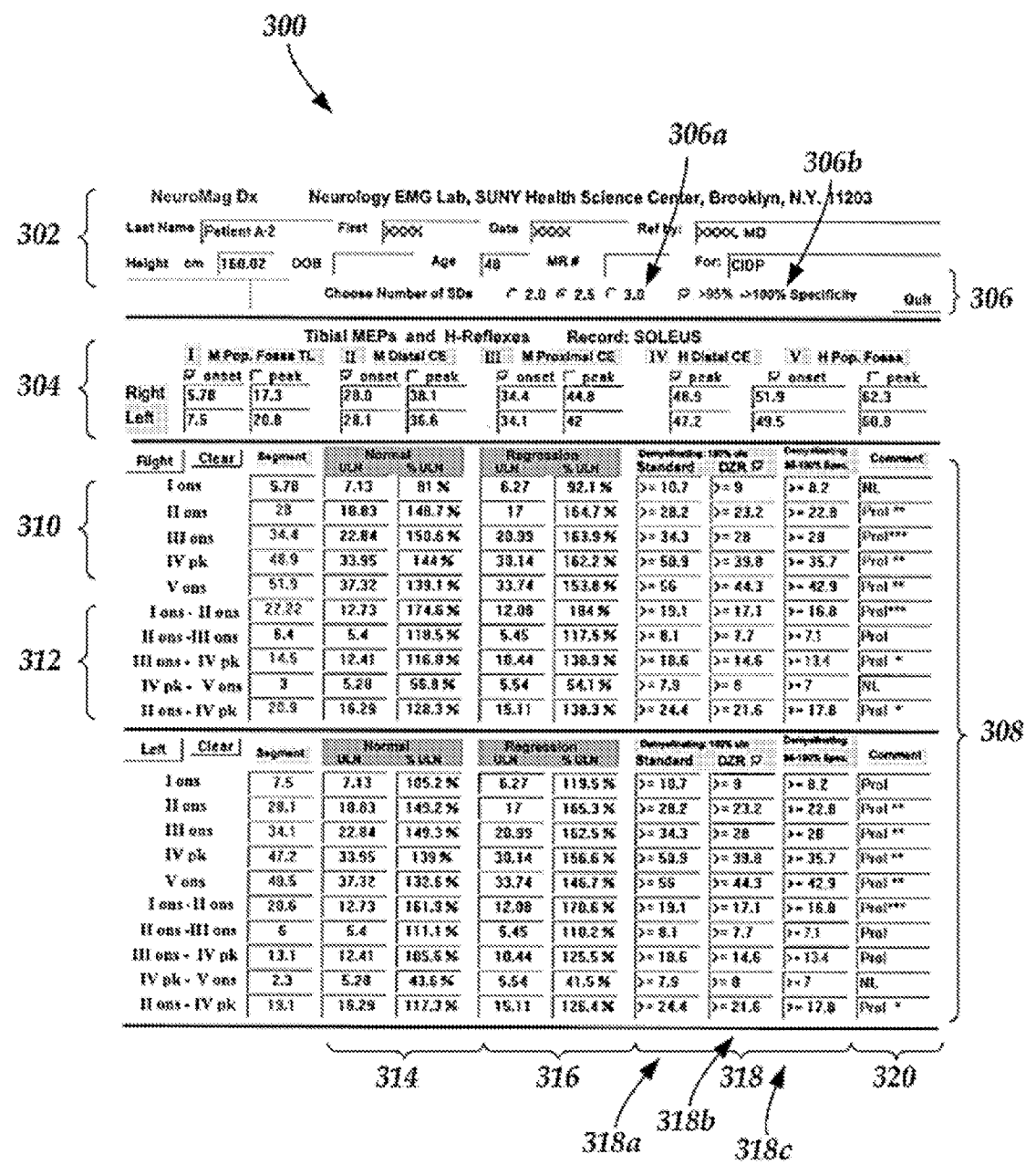

FIG. 3 illustrates one example of an interface 300 (soleus muscle recordings, tibial nerve) that can be displayed on a computer or other device and used for display of results and, optionally, for input of data. The interface 300 includes a patient information section 302 in which information can be entered manually or automatically from another source or any combination thereof. Such information can include one or more of name, date, height, weight, date of birth, age, gender, clinician, and the like.

The interface 300 also includes a CMAP measurement section 304 into which the results of CMAP measurements can be entered. The interface may allow manual entry or may receive the information from another source, such as, for example, a measurement device or a computer or computer-readable media or through wired or wireless transmission, or any combination thereof. In some instances, the interface may be presented on the display of a computer that is part of the measurement device. In other embodiments, the interface may be presented on a display of a computer that is independent of the measurement device.

The CMAP measurement section 304 may present a set of possible CMAP measurements as illustrated in FIG. 3 where the section 304 presents CMAP I, II, III, IV, and V. Other or alternative CMAP measurements may be presented and, in some embodiments, the user may be permitted to select from a set of possible CMAP measurements that can be presented in section 304. Section 304 may also provide boxes (which are optionally selectable) to indicate whether the measurement is for "onset" or "peak", as illustrated in FIG. 3. In some instances, such as CMAP IV, the selectable box for "onset" is not made available because it may not be a viable measurement. In addition, the section 304 may allow the user to select whether the measurements are for latency or conduction velocity. FIG. 3 also indicates that measurements can be provided for both the right soleus and left soleus. It will be understood that, at least in some embodiments, it may not be necessary for the user to enter all of the available measurements, but that entry of a subset of the measurements may be sufficient.

The interface 300 may also include a boundary definition section 306 in which a user can select parameters for the boundary definitions. For example, interface 300 includes a standard deviation section 306a that allows the user to select the number of standard deviations that define the axonal boundary, as described in detail above. The interface 300 also includes a specificity section 306b that allows the user to select a level of specificity (e.g., >95% to <100% or 100%) for use when determining the demyelinating boundary using the specificity approach, as described above. (The 100% specificity values for each parameter are in bold, the >95 to 100% specificity values are not in bold). Other sections can include a percentage section that allows the user to select a percentage (e.g., 120%, 125%, or 150%) for use when determining the demyelinating boundary using the percentage approach, as described above. In other embodiments, values for one or more of these selections may be fixed within the hardware or software or may be selectable through a portion of the hardware or software other than interface 300.

The interface 300 includes a results section 308. The illustrated results section 308 includes results 310 related to each of the CMAP measurement values, as well as results 312 related to a number of parameters calculated from the CMAP measurement values. It will be understood that other embodiments of the interface may include results for more or fewer measurement values and more or fewer parameters.

The interface 300 includes a ULN section 314 where the ULN is based on the predetermined population. The interface 300 also includes a regression ULN section 316 in which the ULN is calculated using analysis from the DZR approach described above. In the illustrated embodiment, a percentage of the ULN (% ULN) is calculated and presented for each of the measurement values and parameters. It will be recognized that other embodiments, may or may not include ULN section 314 or regression ULN section 316. It will also be understood that for an interface that receives conduction velocity information (see, for example, interface 500), LLN will replace ULN in this paragraph.

The interface includes a demyelinating boundary section 318. The illustrated embodiment includes a first demyelinating column 318a that indicates the demyelinating boundary using the percentage approach described above, a second demyelinating column 318b that indicates the demyelinating boundary using the DZR approach described above, and a third demyelinating column 318c that indicates the demyelinating boundary using the specificity approach described above. It will be recognized that other embodiments, may or may not include one or more of the first demyelinating column, second demyelinating column, or third demyelinating column. It will also be understood that for an interface that receives conduction velocity information (see, for example, interface 500), the boundaries will relate to the LLN.

The interface also includes a comment column 320 that evaluates the measurement value or parameter relative to the demyelination boundary or boundaries. In the illustrated embodiment, if a latency is demyelinated according to a specificity latency boundary, it is given one star, and both the input latency being evaluated and the comment appear in red (prol*) (i.e., prolonged). If the input latency is demyelinated according to both specificity and percentage latency boundaries, it is given two stars (input latency and comment also in red), as (prol). If the input latency is demyelinated according to specificity, percentage, and DZR latency boundaries, it is given three stars (input latency and comment also in red), as (prol*). In the illustrated embodiment, "NL" means normal latency. It will be understood that other interfaces may use different schemes for identification of results and may use, for example, "slow" instead of "prol" when the measured value is conduction velocity. In at least some embodiments, if a parameter is "prol" but not within the demyelinating range (i.e. without *, , or *), it can be interpreted as being within the axonal range.

Figure 5:
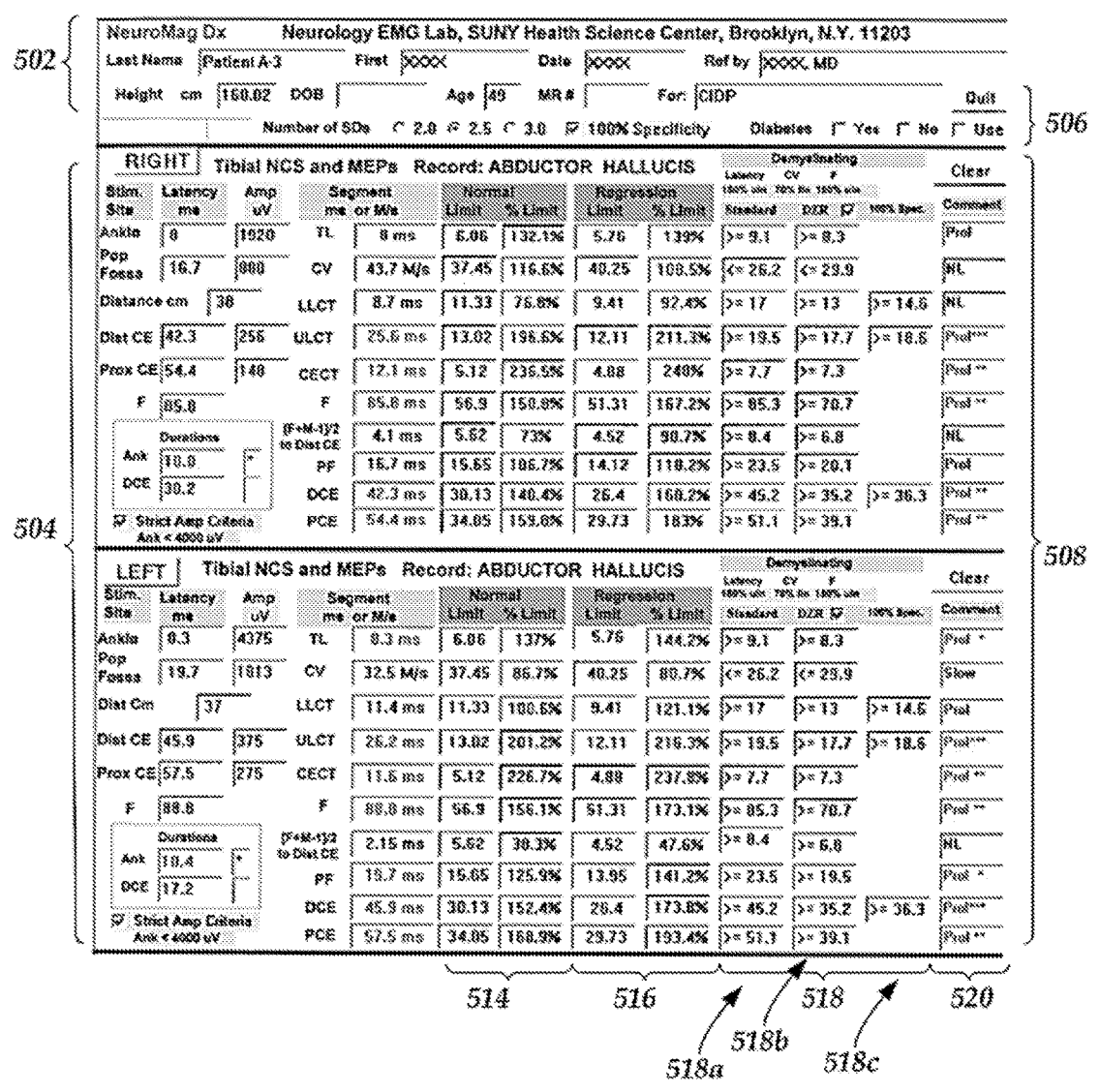
Figure 6:
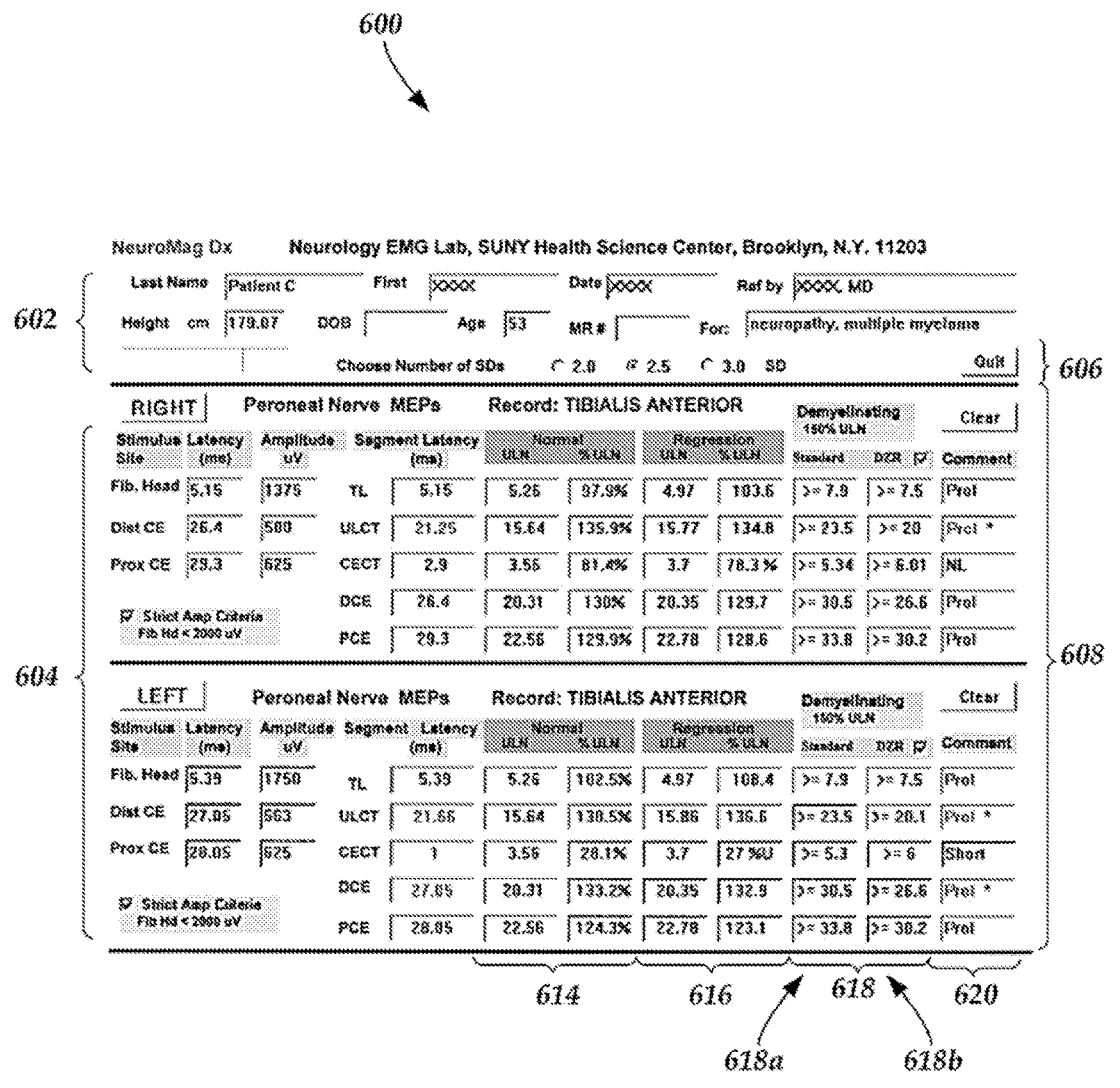

Similar interfaces can be provided for the femoral nerve (FIG. 4), tibial nerve (FIG. 5), and peroneal nerve (FIG. 6). In the illustrated embodiments, only 100% specificity borders are used in the tibial and in the femoral interfaces. The illustrated peroneal interface does not presently have specificity borders because too few patients were evaluated, but other embodiments could include specificity borders.

Figure 4:
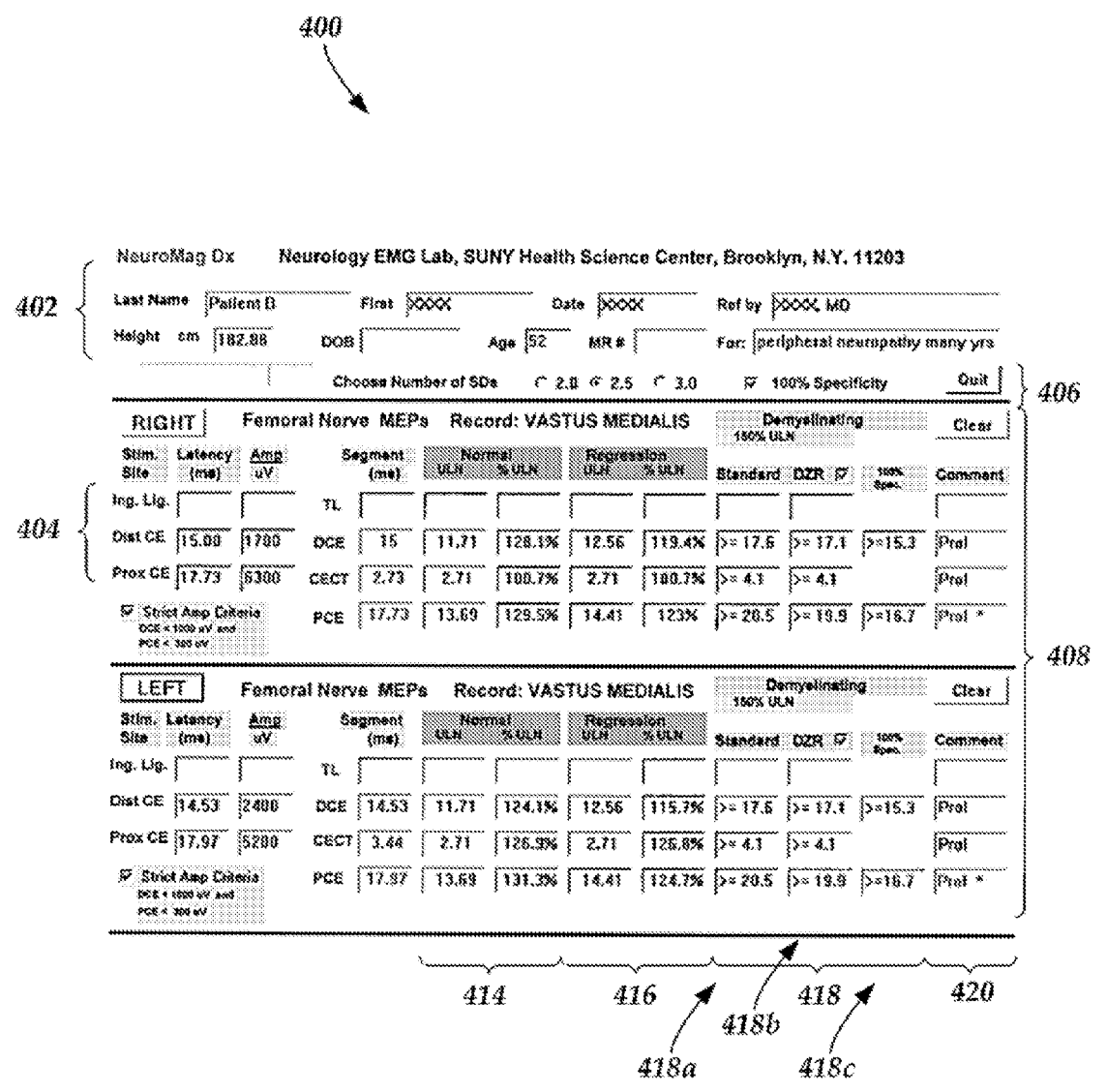

The vastus medialis (femoral nerve) interface 400 of FIG. 4 includes a patient information section 402, CMAP measurement section 404, boundary definition section 406, results section 408 for measurement values (TL=terminal latency from inguinal ligament (not usually obtained), DCE=distal caudal equina, PCE=proximal caudal equina) and calculated parameters (CECT=PCE-DCE), ULN section 414, regression ULN section 416, demyelinating boundary section 418 with first column 418*a* using the percentage approach and second column 418*b* using the DZR approach and third column 418*c* (for select values and parameters) using the specificity approach, and comments section 420. These sections are similar to the corresponding sections in interface 300 of FIG. 3.

The abductor hallucis muscle (tibial nerve) interface 500 of FIG. 5 includes a patient information section 502, CMAP measurement section 504, boundary definition section 506, results section 508 for measurement values (TL=terminal latency from ankle, PF=popliteal fossa, F=F wave latency, DCE=distal caudal equina, PCE=proximal caudal equina) and calculated parameters (CV=conduction velocity, LLCT=lower leg conduction time, ULCT=upper leg conduction time, CECT=cauda equina conduction time), ULN section 514, regression ULN section 516, demyelinating boundary section 518 with first column 518*a* using the percentage approach and second column 518*b* using the DZR approach and third column 518*c* (for select values and parameters) using the specificity approach, and comments section 520. These sections are similar to the corresponding sections in interface 300 of FIG. 3.

Interface 500 uniquely has a non-diabetic vs diabetic information query. In at least some embodiments, if a patient is not diabetic, then the 100% specificity boundary for ULCT within the demyelinating range can be lowered from, for example, 18.6 to 16 msec, which significantly improves sensitivity.

The tibialis anterior muscle (peroneal nerve) interface 600 of FIG. 6 includes a patient information section 602, CMAP measurement section 604, boundary definition section 606, results section 608 for measurement values (TL=terminal latency from the fibula head, DCE=distal caudal equina, PCE=proximal caudal equina) and calculated parameters (ULCT=upper leg conduction time from DCE to TL), CECT=PCE-DCE), ULN section 614, regression ULN section 616, demyelinating boundary section 618 with first column 618*a* using the percentage approach and second column 618*b* using the DZR approach, and comments section 620. These sections are similar to the corresponding sections in interface 300 of FIG. 3.

It is understood that with more clinical experience, some of the normal values may change.

In at least some embodiments, the 400, 500, and 600 interfaces may also show a strict amplitude criteria query. If strict amplitude criteria are selected, then the % ULN for latencies, and % LLN for conduction velocity will automatically select the most conservative condition instead of the less strict condition to define the demyelinating boundary. In at least some embodiments, interface 300 also provides for analysis of negative peak latencies for waves I, II, III, and V, as well as the analysis of onset latencies. This is employed for the occasional situation in which the onset positivity cannot be visually discerned. The use of negative peak latencies may be useful in the presence of extremely prolonged latencies, because the conclusion of extreme prolongation will most likely be correct, but onset latencies are significantly more reliable.

Figure 7:
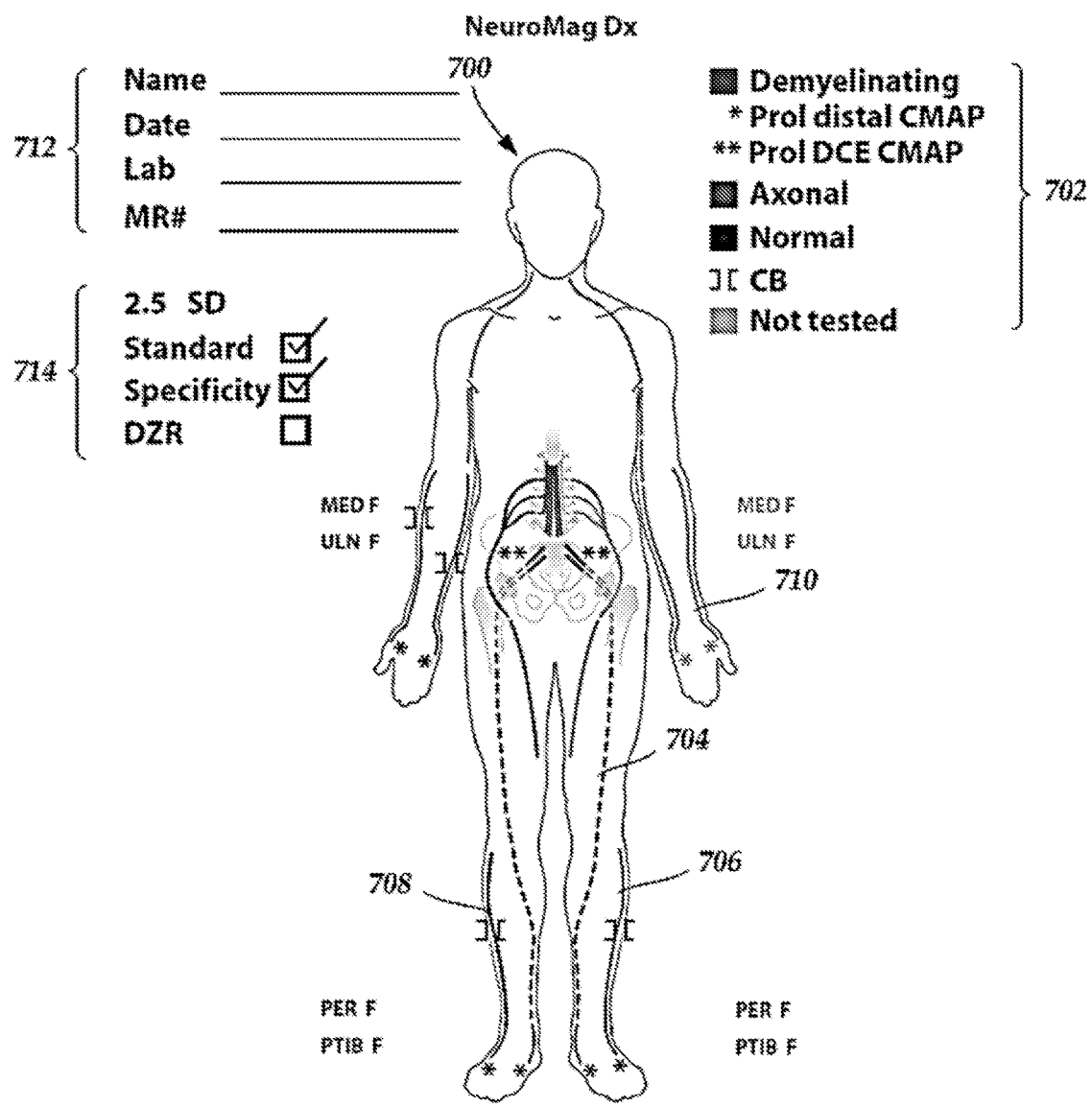
FIG. 7 illustrates one embodiment of a pictorial display of demyelination results, according to some embodiments of the invention.

The information regarding demyelination from any one or more of the interfaces 300, 400, 500, 600 can be displayed pictorially as illustrated in FIG. 7. FIG. 7 presents a pictorial form 700 that depicts an anatomical diagram of the human form (or a portion of the human form) with select nerve pathways, pelvis, long bones, spinal cord, organs, or the like. An optional legend 702 is also provided. The information regarding demyelination from the interfaces 300, 400, 500, 600 can be presented on the pictorial diagram 700 by highlighting nerve pathways or regions of the body where demyelination is indicated. Such highlighting can be performed by, for example, using color (e.g., red for demyelination), using heavier lines, or drawing the nerve pathway or region on the diagram, or any other suitable arrangement which may be indicated in the optional legend. As an example, nerve pathways 704 of the illustrated diagram are highlighted by a red color for demyelination. In some embodiments, nerve pathways may be differently highlighted if they are indicated as being in the axonal range. As an example, nerve pathways 706 of the illustrated form are highlighted in a blue color for the axonal range. Nerve pathways 708 with normal latency can be provided in a black color and those nerve pathways 710 with no information (e.g., testing not performed) are in a gray color.

In FIG. 7, a patient information section 712 may be provided and the types of approaches used in the evaluation can be presented at region 714. In the illustrated example, percentage (or standard) and specificity approaches were used, but not the DZR approach. Also, in the illustrated embodiment, the presence of "prolonged distal CMAP duration" is indicated by the color of the single "asterisk" in two locations in each foot and the presence of prolonged "DCE CMAP duration" is indicated by the color of the double "asterisks" in the two locations in the hip region. The brackets indicate the presence of "conduction block" and presently are implemented for motor conduction studies using electric stimulation in the peripheral nerves that are illustrated (median, ulnar, peroneal, tibial). "Prolonged CMAP duration" elicited when electrically stimulating a nerve distally, or magnetically stimulating a nerve proximally at DCE, and "conduction block" are also abnormalities associated with demyelinating peripheral neuropathy.

The interfaces and pictorial diagrams can be used in a variety of methods for identifying demyelinated nerve pathways and indicating these pathways in pictorial form. These methods can be implemented in software, hardware, or any combination thereof.

Figure 8:
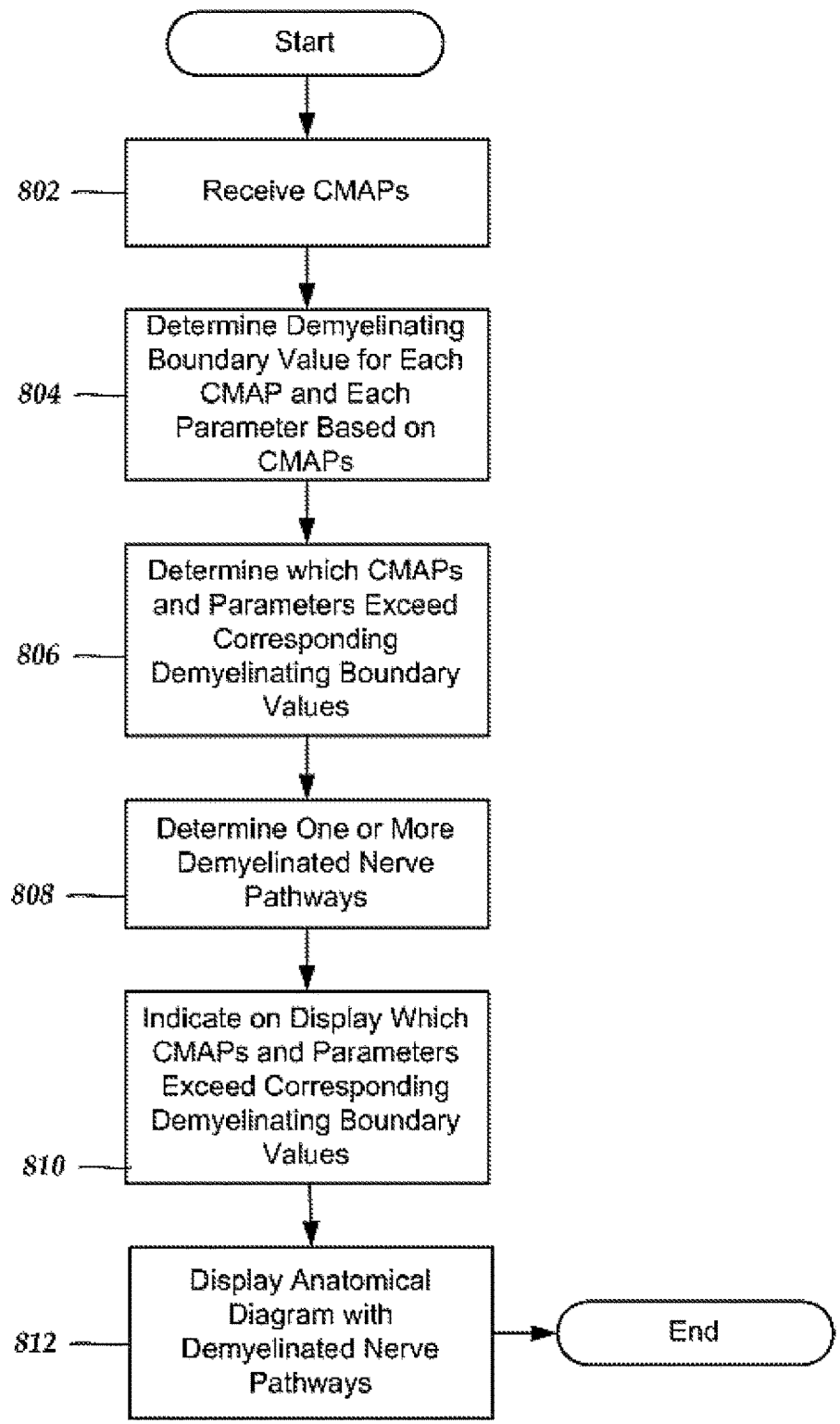
FIG. 8 is a flowchart of one method of identifying and indicating demyelinated nerve pathways, according to some embodiments of the invention.

FIG. 8 is a flowchart of one such method. In step 802, CMAPs are received from a measurement device or from any other source. In step 804, corresponding demyelinating boundary values are determined for the CMAPs and parameters derived from the CMAPs. These boundary values can be determined using one or more of the approaches described above including the percentage approach, the specificity approach, or the DZR approach. In some embodiments, two or more (or even all three of these approaches) can be used to provide a demyelinating boundary value for each approach. It will be understood that these boundary values are not necessarily determined for every CMAP or every parameter or even using every possible approach.

In step 806, it is determined which of the CMAPs and parameters exceed the corresponding demyelinating boundary values. In step 808, it is determined which nerve pathways are demyelinated based on the CMAPs, parameters, and boundary values. In step 810, a display indicates which CMAPs and parameters exceed the corresponding demyelinating boundary values. For example, the display may take the form of any one or more of the interfaces 300, 400, 500, or 600. In step 812, an anatomical diagram is pictorially presented to indicate the demyelinated nerve pathways. FIG. 7 illustrates one example of such an anatomical diagram.

Figure 9:
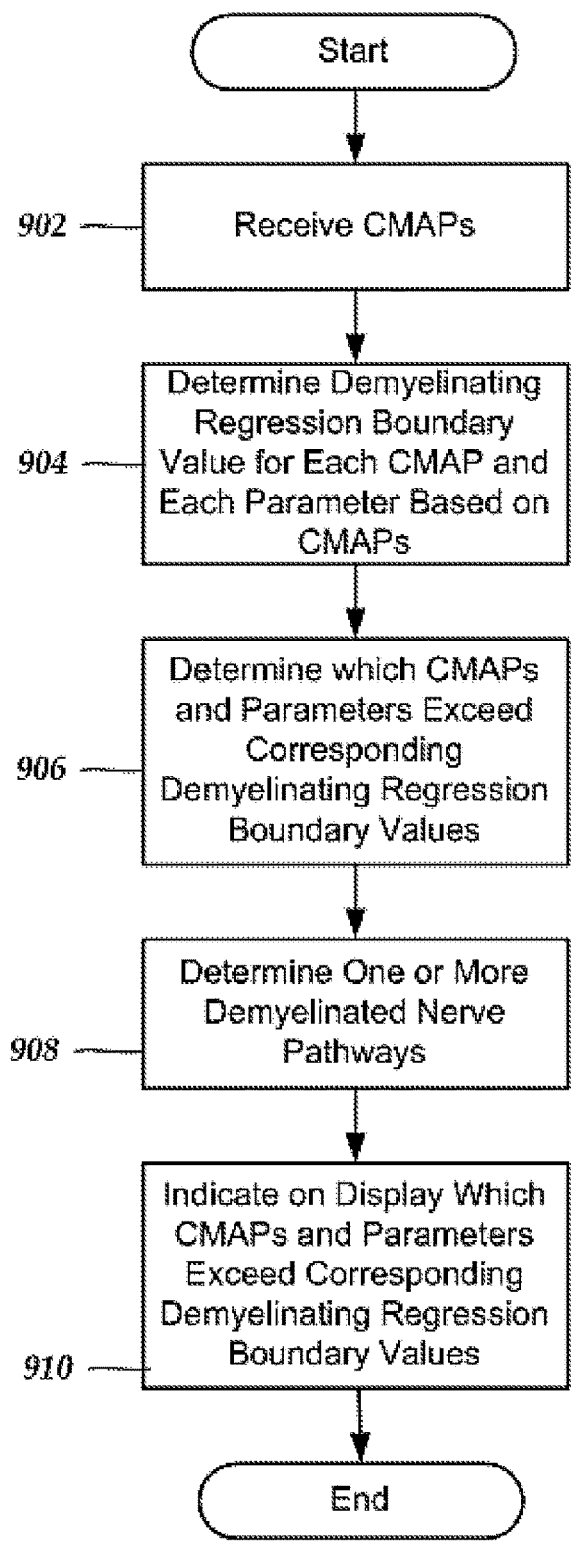
FIG. 9 is a flowchart of one method of identifying and indicating demyelinated nerve pathways, according to some embodiments of the invention.

FIG. 9 is a flowchart of one such method. In step 902, CMAPs are received from a measurement device or from any other source. In step 904, regression analysis, based on at least one of age or height, is used to determine corresponding demyelinating regression boundary values for the CMAPs and parameters derived from the CMAPs. These regression boundary values can be determined using, for example, analysis from the DZR approach described above. It will be understood that these regression boundary values are not necessarily determined for every CMAP or every parameter or even using every possible approach.

In step 906, it is determined which of the CMAPs and parameters exceed the corresponding demyelinating regression boundary values. In step 908, it is determined which nerve pathways are demyelinated based on the CMAPs, parameters, and regression boundary values. In step 910, a display indicates which CMAPs and parameters exceed the corresponding demyelinating regression boundary values. For example, the display may take the form of any one or more of the interfaces 300, 400, 500, or 600. Optionally, an anatomical diagram is pictorially presented to indicate the demyelinated nerve pathways. FIG. 7 illustrates one example of such an anatomical diagram.

It will be understood that each block of the flowchart illustration, and combinations of blocks in the flowchart illustration, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowchart to be performed in parallel. Moreover, some of the steps may also be performed across more than one processor, such as might arise in a multi-processor computer system, a cloud system, a multi-server system, or the like. In addition, one or more blocks or combinations of blocks in the flowchart illustration may also be performed concurrently with other blocks or combinations of blocks, or even in a different sequence than illustrated without departing from the scope or spirit of the invention.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, can be implemented by special purpose hardware based systems, which perform the specified actions or steps, or combinations of special purpose hardware and computer instructions.

The methods, systems, and devices described herein may be embodied in many different forms and should not be construed as limited to the embodiments set forth herein. Accordingly, the methods, systems, and devices described herein may take the form of an entirely hardware embodiment, an entirely software embodiment or an embodiment combining software and hardware aspects. The following detailed description is, therefore, not to be taken in a limiting sense. Systems and devices reference herein typically include mass memory and typically include methods for communication with other devices including mobile devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media that are non-transitory computer-readable media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a processor.

Methods of communication can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and includes any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The invention can be practiced using a computer in any suitable environment including a network environment. It will be understood that the network environment can include a local area network, a wide area network, or any combination thereof. It will also be understood that the network can include device coupled to the network and that there may be multiple devices of each type connected to the network.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A non-transitory computer-readable medium, having computer-executable instructions stored thereon, that in response to execution by a computing device that contains a processor, cause the computing device to perform operations comprising:
receive one or more values from a plurality of compound muscle action potentials (CMAPs), wherein the one or more values is selected from a group consisting of an onset latency, a peak latency, a conduction velocity, a response amplitude measured from a baseline, and a combination thereof;
for each of the one or more values from the plurality of CMAPs, determine a corresponding demyelinating boundary value using a normal value from a preselected population, wherein the corresponding demyelinating boundary value is determined by one or more of the following approaches: (a) a demyelinating Z regression approach, comprising determining a corresponding demyelinating regression boundary value by regression based on at least one of age or height; (b) a percentage approach, comprising determining an upper limit of normal range and determining a corresponding demyelinating percentage boundary value as a percentage value, greater than 100%, of the upper limit of normal range; and (c) a specificity approach, comprising determining a corresponding demyelinating specificity boundary value as a minimum value for which demyelination is determined in the preselected population at a preselected level of specificity, wherein the preselected level of specificity is at least 95%;
determine whether each of the one or more values from the plurality of CMAPs exceeds the corresponding demyelinating boundary value;
determine one or more demyelinated nerve pathways based on which of the one or more values from the plurality of CMAPs exceeds the corresponding demyelinating boundary value;
indicate on an interface each of the one or more values from the plurality of CMAPs and which of the one or more values from the plurality of CMAPs exceed the corresponding demyelinating boundary value for each approach that is used, wherein the interface further evaluates the one or more values relative to the corresponding demyelinating boundary value for each approach; and
display, in pictorial form, an anatomical diagram indicating the one or more demyelinated nerve pathways on the interface.

2. The non-transitory computer-readable medium of claim 1, wherein determining the upper limit of normal range comprises selecting a number of standard deviations and determining the upper limit as a value corresponding to a mean for the preselected population plus the number of standard deviations for the preselected population.

3. The non-transitory computer-readable medium of claim 1, wherein the pre-selected level of specificity is 100%.

4. The non-transitory computer-readable medium of claim 1, wherein the operations further comprise, for each of the one or more values from the plurality of CMAPs, determine a corresponding axonal boundary value using a normal value for the preselected population.

5. The non-transitory computer-readable medium of claim 1, wherein an axonal range is between an axonal boundary value and the corresponding demyelinating boundary value and wherein the operations further comprise displaying on the anatomical diagram which of the one or more demyelinated nerve pathways are in the axonal range.

6. The non-transitory computer-readable medium of claim 1, wherein the plurality of CMAPs comprises a plurality of soleus CMAPs.

7. The non-transitory computer-readable medium of claim 1, wherein the plurality of CMAPs comprises at least one CMAP selected from a femoral CMAP, a tibial CMAP, or a peroneal CMAP.

8. The non-transitory computer-readable medium of claim 1, wherein the plurality of CMAPs is recorded at a soleus, abductor hallucis *brevis*, or a combination thereof.

9. The non-transitory computer-readable medium of claim 1, wherein the plurality of CMAPs comprises at least one CMAP elicited by neuromagnetic stimulation.

10. The non-transitory computer-readable medium of claim 9, wherein the plurality of CMAPs comprises at least one CMAP elicited by neuromagnetic stimulation of a distal cauda equina.

11. The non-transitory computer-readable medium of claim 1, wherein the corresponding demyelinating boundary value is determined by two or more of the demyelinating Z regression approach, the percentage approach, and the specificity approach.

12. The non-transitory computer-readable medium of claim 11, wherein the corresponding demyelinating boundary value is determined by each of the demyelinating Z regression approach, the percentage approach, and the specificity approach.

13. A computer-based method, wherein a plurality of actions is performed by a processor operating within a computing device, the plurality of actions comprising:
receiving one or more values from a plurality of compound muscle action potentials (CMAPs), wherein the one or more values is selected from a group consisting of an onset latency, peak latency, conduction velocity, a response amplitude measured from a baseline, and a combination thereof;
for each of the one or more values from the plurality of CMAPs, determining a corresponding demyelinating boundary value using a normal value from a preselected population, wherein the corresponding demyelinating boundary value is determined by one or more of the following approaches: (a) a demyelinating Z regression approach, comprising determining a corresponding demyelinating regression boundary value by regression based on at least one of age or height; (b) a percentage approach, comprising determining an upper limit of normal range and determining a corresponding demyelinating percentage boundary value as a percentage value, greater than 100%, of the upper limit of normal range; and (c) a specificity approach, comprising determining a corresponding demyelinating specificity boundary value as a minimum value for which demyelination is determined in the preselected population at a preselected level of specificity, wherein the preselected level of specificity is at least 95%;
determining whether each of the one or more values from the plurality of CMAPs exceeds the corresponding demyelinating boundary value;
determining one or more demyelinated nerve pathways based on which of the one or more values from the plurality of CMAPs exceeds the corresponding demyelinating boundary value;
indicating on an interface each of the one or more values from the plurality of CMAPs and which of the one or more values from the plurality of CMAPs exceed the corresponding demyelinating boundary value for each approach that is used, wherein the interface further evaluates the one or more values relative to the corresponding demyelinating boundary value for each approach; and displaying, in pictorial form, an anatomical diagram indicating the one or more demyelinated nerve pathways on the interface.

14. The computer-based method of claim 13, wherein the plurality of CMAPs is recorded at a soleus, abductor hallucis brevis, or a combination thereof.

15. The computer-based method of claim 13, wherein the plurality of CMAPs comprises at least one CMAP elicited by neuromagnetic stimulation.

16. The computer-based method of claim 15, wherein the plurality of CMAPs comprises at least one CMAP elicited by neuromagnetic stimulation of a distal cauda equina.

17. The computer-based method of claim 13, wherein the corresponding demyelinating boundary value is determined by two or more of the demyelinating Z regression approach, the percentage approach, and the specificity approach.

18. The computer-based method of claim 17, wherein the corresponding demyelinating boundary value is determined by each of the demyelinating Z regression approach, the percentage approach, and the specificity approach.

* * * * *